United States Patent [19]

Yoshinaka et al.

[11] 4,029,560
[45] June 14, 1977

[54] PROCESS FOR PRODUCING α,α,α,α',α',α'-HEXACHLOROXYLENE

[75] Inventors: Shigeo Yoshinaka; Masaharu Doya; Seiiji Uchiyama; Sadao Nozaki, all of Niigata, Japan

[73] Assignee: Mitsubishi Gas Chemical Company, Inc., Tokyo, Japan

[22] Filed: Mar. 29, 1976

[21] Appl. No.: 671,698

[30] Foreign Application Priority Data

Apr. 1, 1975   Japan ............................. 50-39587

[52] U.S. Cl. .................... 204/163 R; 260/544 D
[51] Int. Cl.$^2$ ........................................ B01J 1/10
[58] Field of Search ............................... 204/163 R

[56] References Cited

UNITED STATES PATENTS 3,836,445   9/1974   Sano et al. .................... 204/163 R

FOREIGN PATENTS OR APPLICATIONS 583,634   12/1946   United Kingdom ........... 240/163 R

OTHER PUBLICATIONS

Clippinger, Chem. Abs., vol. 75, 109648s (1971).

Yamagiwa et al., Chem. Abs., vol. 81, 170326w (1975).

*Primary Examiner*—Leland A. Sebastian
*Attorney, Agent, or Firm*—Wenderoth, Lind & Ponack

[57] ABSTRACT

This invention concerns to a process for α,α,α,α',α',α'-hexachloroxylene by reacting m-xylene or p-xylene or a partially chlorinated product thereof with chlorine under the irradiation of ultraviolet rays, the process comprising (1) a first-step chlorination reaction which is carried out in the presence of α,α,α,α',α',α'-hexachloroxylene as a solvent added at the initial stage of the reaction, and continued until a compound convertible to α,α,α,α',α',α'-hexachloroxylene by chlorination becomes substantially absent in the reaction mixture, and (2) a second-step chlorination reaction which is continued from the first-step chlorination and carried out to convert difficulty-separable by-products present in the reaction mixture to easily-separable compounds. This invention also concerns to a process for producing an aromatic dicarboxylic acid chloride which comprise reacting the resulting α,α,α,α',α',α'-hexachloroxylene with isophthalic acid or terephthalic acid.

5 Claims, No Drawings

PROCESS FOR PRODUCING α,α,α,α',α',α'-HEXACHLOROXYLENE

FIELD OF THE INVENTION

This invention relates to a process for producing α,α,α,α',α',α'-hexachloroxylene of high purity, and more specifically, to a process for producing α,α,α,α',α',α'-hexachloroxylene especially suitable as a raw material for preparing aromatic dicarboxylic acid chlorides having high quality and to a process for fproducing aromatic dicarboxylic acid chlorides of high quality from the hexachloroxylene.

BACKGROUND OF THE INVENTION

In recent years, wholly aromatic polyamides or wholly aromatic polyesters have been receiving widespread attention as thermally stable polymers having superior properties, and accordingly, the importance of isophthaloyl dichloride or terephthaloyl dichloride as a raw material for these polyamides or polyesters has remarkably increased. The isophthaloyl dichloride or terephthaloyl dichloride used for this purpose, however, is required to have high purity. Various methods have been suggested for producing the isophthaloyl dichloride or terephthaloyl dichloride, and among them, a method for producing isophthaloyl dichloride or terephthaloyl dichloride which comprises chlorinating m-xylene or p-xylene or a compound resulting from the partial chlorine-substitution of its methyl groups to form α,α,α,α',α',α'-hexachloroxylene, and reacting the resulting hexachloro-xylene with isophthalic acid or terephthalic acid is especially advantageous from an economic standpoint. The reactions in this method are schematically shown by the following reaction equations (I) and (II).

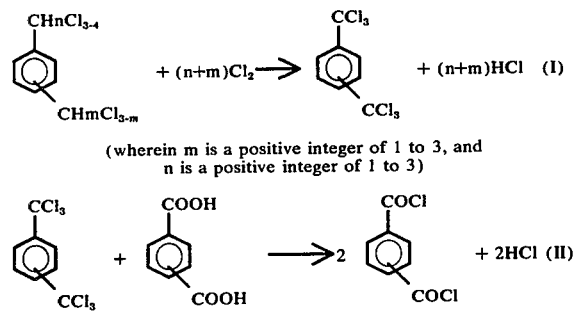

(wherein m is a positive integer of 1 to 3, and n is a positive integer of 1 to 3)

We have extensively studied the method of producing aromatic dicarboxylic acid chlorides in accordance with equations (I) and (II), and found that the quality of the hexachloroxylene exerts a great influence on the quality of the aromatic dicarboxylic acid chlorides produced by the above method, and therefore, hexachloroxylene of high purity is especially desired for the production of high quality aromatic dicarboxylic acid chlorides as raw materials for thermally stable polymers.

Hexachloroxylene is prepared by a side chainchlorination reaction of xylene or a compound resulting from the partial chlorine-substitution of its methyl groups. Known methods for its production include the chlorination of xylene or a compound resulting from the partial chlorine-substitution of its methyl groups in the liquid phase by irradiation of light, or in the presence of a peroxide such as benzoyl peroxide. However, according to these methods, impurities such as a compound resulting from the direct substitution of chlorine at the benzene nucleus of xylene, or tarry materials are formed as by-products, or chlorinating decomposition or coloration frequently incidental to chlorination occurs. Consequently, the yield of the product is reduced, and long periods of time are required for the reaction, with the result that the quality or purity of the desired product is adversely affected. When hexachloroxylene containing such impurities is used as a raw material, it is difficult to prepare aromatic dicarboxylic acid chlorides having high quality feasible for use as a raw material for thermally stable polymers.

It is known to use carbon tetrachloride as a solvent, or add an alkylene polyamine, benzamide, acetamide, an aryl phosphate or sorbitol, so as to inhibit the formation of undesirable impurities. These methods contribute to some extent to the improvement of the quality of hexachloroxylene, but to no satisfactory degree. U.S. Pat. No. 2,810,688, on the other hand, discloses a process for inhibiting undesirable side-reactions which comprises continuously contacting xylene or a compound resulting from the partial chlorine-substitution of its methyl groups with a chlorine-containing gaseous stream in the liquid phase under the irradiation of light in a multiple of stages to perchlorinate the side-chain methyl groups by passing the xylene and the chlorine-containing gaseous stream countercurrent to each other. This method, however, is still unable to afford hexachloroxylene of satisfactory purity.

We previously found that the undesirable side-reactions take place mainly in the initial stage of the reaction, and that the use of the same hexachloroxylene as the final product as a solvent can effectively inhibit the undesirable side-reactions, and based on this finding, proposed a process for producing hexachloroxylene which comprises reacting xylene or a compound resulting from the partial chlorine-substitution of its methyl groups with chlorine under the irradiation of light to perchlorinate its side-chain methyl groups wherein α,α,α,α',α', α'-hexachloroxylene as a final product is caused to be present in the reaction system from the initial stage of the reaction so as to inhibit side reactions. This process is covered by our copending U.S. patent application Ser. No. 504,989. This method makes it possible to obtain hexachloroxylene having markedly improved purity. We have, however, found that the purity of the hexachloroxylene obtained by this method is still not entirely satisfactory for use as a material for producing aromatic dicarboxylic acid chlorides which are raw materials for producing thermally stable polymers, and requires further improvement.

A customary purifying method such as distillation or recrystallization could be employed so as to improve the purity of the hexachloroxylene, but cannot solve the problem of obtaining hexachloroxylene having such a very high purity. When it is desired to purify hexachloroxylene by distillation, it is difficult to separate impurities from hexachloroxylene obtained by the conventional method because these impurities have boiling points close to the boiling point of the hexachloroxylene. Purification of hexachloroxylene by recrystallization, on the other hand, cannot afford hexachloroxylene of the desired purity at low cost; namely, since hexachloroxylene is readily soluble in organic solvents (especially in the case of α,α,α,α',α', α'-hexachloro-m-xylene, its low melting point jointly becomes a problem), a large quantity of the desired final product is lost. The recrystallization method is therefore less advantageous than the distillation method.

It is an object of this invention to provide a process for producing hexachloroxylene of high purity suitable for use as a raw material for the preparation of aromatic dicarboxylic acid chlorides of high quality.

Another object of this invention is to provide a process for producing aromatic dicarboxylic acid chlorides having such a high quality as is required of a raw material for thermally stable polymers using such a high purity hexachloroxylene as a starting material.

SUMMARY OF THE INVENTION

The present invention provides a process for batchwise or continuous production of $\alpha,\alpha,\alpha,\alpha',\alpha',\alpha'$-hexachloroxylene by reacting a xylene compound selected from the group consisting of (i) xylene selected from m-xylene and p-xylene and (ii) compounds resulting from the partial chlorination of the side-chain methyl groups of the xylene (i), with chlorine under the irradiation of ultraviolet rays; said process comprising 1. a first-step chlorination reaction which is carried out in the presence of $\alpha,\alpha,\alpha,\alpha',\alpha',\alpha'$-hexachloroxylene as a solvent added at the initial stage of the reaction, and continued until a compound convertible to $\alpha,\alpha,\alpha,\alpha',\alpha',\alpha'$-hexachloroxylene by chlorination becomes substantially absent in the reaction mixture, and 2. a second-step chlorination reaction which is continued from the first-step chlorination and carried out to convert difficultly-separable by-products present in the reaction mixture to easily-separable compounds.

The invention also provides a process for producing isophthaloyl dichloride or terephthaloyl dichloride which comprises reacting the high purity $\alpha,\alpha, \alpha,\alpha',\alpha'\lambda,\alpha'$-hexachloro-m-xylene or $\alpha,\alpha,\alpha,\alpha',\alpha',\alpha'$-hexachloro-p-xylene with isophthalic acid or terephthalic acid respectively in a manner known per se.

DETAILED DESCRIPTION OF THE INVENTION

The process of this invention includes both a process for producing $\alpha,\alpha,\alpha,\alpha',\alpha',\alpha'$-hexachloro-m-xylene which comprises chlorinating m-xylene or a compound resulting from the partial chlorine-substitution of its methyl groups to perchlorinate the methyl groups, and a process for producing $\alpha,\alpha,\alpha,\alpha',\alpha',\alpha'$-hexachloro-p-xylene which comprises chlorinating p-xylene or a compound resulting from the partial chlorine-substitution of its side-chain methyl groups to perchlorinate the side-chain methyl groups. For the sake of brevity, m-xylene and p-xylene is sometimes referred to simply as "xylene" in the present application. The "compound resulting from the partial chlorine-substitution of its side-chain methyl groups" denotes a compound resulting from the chlorination of at least one methyl group of xylene, and includes, for example, $\alpha$-monochloro-m-xylene, $\alpha,\alpha'$-dichloro-m-xylene, $\alpha$-monochloro-p-xylene, or $\alpha,\alpha'$-dichloro-p-xylene. These compounds resulting from the partial chlorination of the methyl groups of xylene can be converted to $\alpha,\alpha,\alpha,\alpha',\alpha', \alpha'$-hexachloroxylene, the desired product in the present invention, by further chlorination of the chlorinated side-chain methyl groups unless their benzene nucleus is directly substituted by chlorine. Hence, the term "compound convertible to $\alpha,\alpha,\alpha,\alpha',\alpha',\alpha'$-hexachloroxylene by chlorination", as used in the present application, is meant to include xylene (m-xylene or p-xylene) and compounds derived from xylene in which the benzene nucleus is not chlorinated, but the side-chain methyl groups are partly chlorinated.

The process of this invention comprises the main chlorination reaction in the first step, and the post chlorination in the second step successively performed after the first step. In the first-step main chlorination reaction, m-xylene or p-xylene or a compound resulting from the partial chlorine-substitution of its methyl groups is reacted with chlorine under the irradiation of light containing ultraviolet rays. The reaction in this stage is carried out in the presence of, as a solvent, $\alpha,\alpha,\alpha,\alpha',\alpha',\alpha'$-hexachloroxylene, the same as the final product, from the outset of the reaction, that is, the initial reaction stage where up to one chlorine atom is introduced per side-chain methyl group of xylene, and continued until "a compound convertible to $\alpha,\alpha,\alpha,\alpha', \alpha',\alpha'$-hexachloroxylene by chlorination" becomes substantially absent in the reaction mixture. Since at the end of this main chlorination reaction, substantially all of the "compound convertible to $\alpha,\alpha,\alpha,\alpha',\alpha',\alpha'$-hexachloroxylene by chlorination" has been converted to $\alpha,\alpha,\alpha,\alpha',\alpha',\alpha'$-hexachloroxylene, there is no further formation of $\alpha,\alpha, \alpha,\alpha',\alpha',\alpha'$-hexachloroxylene on continuing the chlorination reaction. The first-step main chlorination reaction is substantially the same as the process disclosed in our copending U.S. patent application Ser. No. 504,989, and the process of this U.S. Application consisting only of the first-step main chlorination reaction. Since the yield of $\alpha,\alpha,\alpha,\alpha',\alpha',\alpha'$-hexachloroxylene as a final product can never increase, if it may decrease, even when the chlorination is continued after the end of the first-step main chlorination reaction, it is reasonable to think that continuation of the chlorination reaction is not required as far as the preparation of $\alpha,\alpha,\alpha,\alpha', \alpha'$, $\alpha'$-hexachloroxylene is concerned. From this viewpoint, in the process of U.S. patent application Ser. No. 504,989, the reaction is stopped when the first-step main chlorination reaction has ended.

We have now found that $\alpha,\alpha,\alpha,\alpha',\alpha',\alpha'$-hexachloroxylene obtained by the first-step main chlorination reaction still contains small amounts of impurities which are difficult to separate by a separating procedure such as distillation, and that when an aromatic dicarboxylic acid chloride is prepared from the $\alpha,\alpha,\alpha,\alpha',\alpha',\alpha'$-hexachloroxylene obtained only by the first-step main chlorination reaction and used as a raw material for thermally stable polymers, the inclusion of these impurities in the hexachloroxylene even in small amounts adversely affects the preparation of the thermally stable polymers. Our investigations made in an attempt to remove such undesirable impurities led to the discovery that when a second-step chlorination reaction (which is referred to in the present application as a post chlorination reaction) is carried out subsequent to the first-step main chlorination reaction, usually under milder reaction conditions than in the first-step reaction, the impurities can be converted to easily removable compounds, and as a result, $\alpha,\alpha,\alpha,\alpha',\alpha',\alpha'$-hexachloroxylene having a higher purity than the $\alpha,\alpha,\alpha,\alpha',\alpha',\alpha'$-hexachloroxylene prepared only by the first-step main chlorination reaction can be obtained.

Of the side-reactions which take place mainly in the initial stage of the reaction, the formation of a compound resulting from the substitution of chlorine directly at the benzene nucleus of xylene is most troublesome. Since chlorine introduced into a benzene nucleus cannot be removed under the reaction conditions, such a compound having chlorine substituted directly at the benzene nucleus cannot be converted to $\alpha,\alpha,\alpha,\alpha',\alpha'$, $\alpha'$-hexachloroxylene by further chlorination.

The second-step post chlorination reaction in this invention is described specifically below with reference to the production of $\alpha,\alpha,\alpha,\alpha',\alpha',\alpha'$-hexachloro-m-xylene by chlorination of m-xylene as an example. This description is for the purpose of facilitating the understanding of the present invention, and is not intended in any way to limit the present invention.

The first-step main chlorination reaction of perchlorinating the methyl groups of xylene to form $\alpha,\alpha,\alpha,\alpha',\alpha',\alpha'$-hexachloroxylene is a sequential chlorination of the methyl groups, and is considered to proceed in accordance with the following equation (III). Equation (III) shows only main intermediates (partially chlorinated products). In fact, other intermediates not shown in equation (III) would also occur although in small amounts, but the indication of such intermediates is omitted in order to avoid the complexitity of the description.

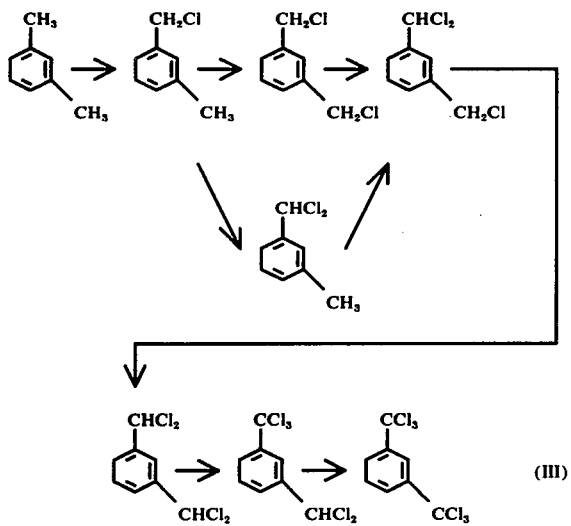

(III)

On the other hand, the formation of a monochloro-nucleus-substituted produce represented by equation (IV) is a main side-reaction in the early stage of the reaction. A by-product resulting from the substitution of two or more chlorine atoms at the benzene nucleus of m-xylene, even if formed, would be in a far smaller amount than the monochloro-nucleus-substituted product.

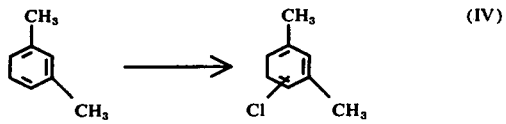

(IV)

The monochloro-nucleus-substituted product formed in the initial stage of the reaction is further chlorinated as the reaction proceeds. But no further introduction of chlorine into the benzene nucleus occurs at this time, and only its side-chain methyl groups would be sequentially chlorinated in the same manner as shown in equation (III).

In the initial stage of the main chlorination reaction in the first step, $\alpha,\alpha,\alpha,\alpha',\alpha',\alpha'$-hexachloroxylene as a final product is not yet formed, and the "compound convertible to $\alpha,\alpha,\alpha,\alpha',\alpha',\alpha'$-hexachloroxylene by chlorination" present in the reaction mixture consists mainly of the starting xylene and a compound resulting from the chlorine-substitution of its side chain methyl groups to a low degree. With the progress of the reaction, the concentrations of the starting xylene and the low degree chlorine-substituted xylene decrease, and the concentrations of compounds chlorine-substituted to a higher degree increase. Near the end of the first-step main chlorination reaction, the "compound convertible to $\alpha,\alpha,\alpha,\alpha',\alpha',\alpha'$-hexachloroxylene by chlorination" consists substantially of $\alpha,\alpha,\alpha,\alpha',\alpha'$-pentachloroxylene. The time when substantially all of the $\alpha,\alpha,\alpha,\alpha',\alpha'$-pentachloroxylene present in the reaction mixture has been converted to $\alpha,\alpha,\alpha,\alpha',\alpha',\alpha'$-hexachloroxylene on further proceeding of the reaction is the end of the first-step main chlorination reaction. Accordingly, whether or not the main chlorination reaction has been completed can be known by determining the residual $\alpha,\alpha,\alpha,\alpha'$, $\alpha'$-pentachloroxylene in the reaction mixture by a suitable analyzing method such as gas-chromatography.

The by-product monochloro-nucleus-substituted product formed in the initial stage of the main chlorination reaction in the first step is succenssively chlorinated at its side-chain methyl groups, and at the end of the first-step main chlorination reaction, it is converted mainly to a monochloro-nucleus-substituted product of $\alpha,\alpha,\alpha,\alpha',\alpha'$-pentachloroxylene and a monochloro-nucleus-substituted product of $\alpha,\alpha,\alpha,\alpha',\alpha',\alpha'$-hexachloroxylene. The monochloro-nucleus-substituted product of $\alpha,\alpha,\alpha,\alpha'$, $\alpha',\alpha'$-hexachloroxylene has a boiling point considerably different from that of $\alpha,\alpha,\alpha,\alpha',\alpha',\alpha'$-hexachloroxylene as a final product, and is relatively easy to separate by distillation. However, the monochloro-nucleus-substituted product of $\alpha,\alpha,\alpha,\alpha',\alpha'$-pentachloroxylene has a boiling point very close to that of the final product, and is extremely difficult to separate by distillation. In order, therefore, to increase the purity of $\alpha,\alpha,\alpha,\alpha'$, $\alpha',\alpha'$-hexachloroxylene as a final product, it is very important to minimize the amount of the monochloro-nucleus-substituted product of $\alpha,\alpha,\alpha,\alpha',\alpha'$-pentachloroxylene present in the reaction mixture which is obtained on completion of the main chlorination reaction in the first step.

The characteristic feature of the present invention is that after the completion of the first-step main chlorination reaction, the second-stage post chlorination is performed to convert the monochloro-nucleus-substituted product of $\alpha,\alpha,\alpha,\alpha',\alpha'$-pentachloroxylene present in the reaction mixture to a monochloro-nucleus-substituted product of $\alpha,\alpha,\alpha,\alpha',\alpha',\alpha'$-hexachloroxylene which is easily separable.

Thus, the second-stage post chlorination reaction performed in the present invention is carried out in order to convert difficultly -separable by-products (mainly, the monochloro-nucleus-substituted product of $\alpha,\alpha,\alpha,\alpha',\alpha'$-pentachloroxylene) to readily separable compounds (mainly, the monochloro-nucleus-substituted product of $\alpha,\alpha,\alpha,\alpha'$, $\alpha'$, $\alpha'$-hexachloroxylene) while the desired $\alpha,\alpha,\alpha,\alpha',\alpha'$, $\alpha'$-hexachloroxylene remains unchanged. If the reaction conditions in the second-step post chlorination are severe, a reaction of substituting chlorine at the benzene nucleus of the desired $\alpha,\alpha,\alpha,\alpha',\alpha',\alpha'$-hexachloroxylene occurs simultaneously. This reaction reduces the yield of the desired final product, and should be avoided. In order to inhibit such undesirable side-reactions to the greatest possible extent and to allow only the perchlorination of the methyl groups of a compound resulting from the chlorination of the benzene nucleus of xylene and the partial chlorination of its side-chain methyl groups to take place selectively as intended by the second-step post chlorination reaction, the reaction conditions in the second-step post chlorination are preferably milder than those employed in the first-step main chlorination reaction. This can be effectively achieved especially by reducing the chlorine concentration in the reaction system.

According to the process of this invention, the amount of the monochloro-nucleus-substituted product of $\alpha,\alpha,\alpha,\alpha',\alpha'$-pentachloroxylene present as an impurity in the desired final product can be reduced by the second-step post chlorination reaction. This is especially of great significance when an aromatic dicarboxylic acid chloride is prepared from the $\alpha,\alpha,\alpha,\alpha',\alpha',\alpha'$-hexachloroxylene in accordance with equation (II), and is used for the preparation of thermally stable polymers. If the above impurity is present in the starting $\alpha,\alpha,\alpha,\alpha', \alpha', \alpha'$-hexachloroxylene, the degree of polymerization of the polymer finally obtained decreases. The reduction in the degree of polymerization is probably because in the reaction of equation (II), the monochloro-nucleus-substituted product of $\alpha,\alpha,\alpha,\alpha',\alpha'$-pentachloroxylene present as an impurity in the reaction system is converted to

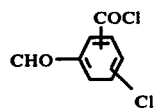

which is mixed as an impurity in the resulting aromatic dicarboxylic acid chloride and causes a reduction in the degree of polymerization of the resulting thermally stable polymer.

Both the first-step main chlorination reaction and the second-step post chlorination reaction in accordance with this invention are carried out under the irradiation of light containing ultraviolet rays. The light containing ultraviolet rays means natural sun's rays or light containaing ultraviolet rays such as a mercury vapor lamp.

The hexachloroxylene to be caused to be present in the reactive system as a solvent from the initial stage of the main chlorination reaction is $\alpha, \alpha, \alpha, \alpha', \alpha', \alpha'$-hexachloro-m-xylene when the desired final product is $\alpha, \alpha, \alpha, \alpha', \alpha', \alpha'$-hexachloro-m-xylene, and $\alpha, \alpha, \alpha, \alpha', \alpha', \alpha'$-hexachloro-p-xylene when the desired final product is $\alpha, \alpha, \alpha, \alpha', \alpha', \alpha'$-hexachloro-p-xylene. The amount of the hexachloroxylene added as a solvent differs depending upon whether the reaction is carried out batchwise or continuously. In the case of the batchwise operation, the amount of the hexachloroxylene solvent is 0.3 to 15 parts by weight, preferably 0.8 to 5 parts by weight, per part by weight of xylene or a compound resulting from the partial chlorine-substitution of its methyl groups. In the case of the continuous operation, the xylene or a compound resulting from the partial chlorine-substitution of its methyl groups is fed so that the cencentration of the hexachloroxylene in the reaction mixture in the reactor becomes 40 to 90% by weight, preferably 70 to 99% by weight.

The reaction temperatures employed in the first-step main chlorination reaction is generally 80° to 160° C for m-xylene or a compound resulting from the partial chlorine-substitution of its methyl groups, and 110° to 160° C for p-xylene or a compound resulting from the partial chlorine-substitution of its methyl groups. But in order to increase the yield of the hexachloroxylene by inhibiting the side-reactions and also to inhibit the formation of impurities which hamper the purification of the hexachloroxylene, the chlorination reaction temperature is preferably 100° to 150° C for m-xylene or the compound resultinf from the partial chlorine-substitution of its methyl groups, and 120° to 150° C for p-xylene or the compound resulting from the partial chlorine-substitution of its methyl groups. The reaction time employed in the main chlorination reaction differs according to the rate of introducing chlorine and the nature of the apparatus, but is usually 7 to 60 hours.

The amount of chlorine to be introduced in the main chlorination reaction differs according to the method of introducing chlorine and the nature of the apparatus, but is usually 0.3 to 2 mole/hour per mole of the xylene or the compound resulting from the partial chlorine-substitution of its methyl groups present before the initiation of the reaction in the case of a batchwise operation; and 1 to 10 moles/hour per mole of xylene or the compound resulting from the partial chlorine-substitution of its methyl groups to be fed to the reactor in the case of a continuous operation. The amount of chlorine may be a large excess, but sufficiently, 100 to 160% of the theoretical amount. In order to increase the reaction efficiency, chlorine is desirably dispersed in the reaction mixture in the form of bubbles which are as fine as possible.

As required, in the first-step main chlorination reaction, a substance for inhibiting the adverse effects of the entry of metallic compounds, such as an alkylene polyamine, benzamide, acetamide, an aryl phosphate or sorbitol, or a catalyst, may be added to the reaction mixture.

After the first-stage chlorination is substantially over, the second-step post chlorination is successively carried out. The reaction time employed in the post chlorination reaction is desirably 0.5 to 3 hours. In the second step, the amount of chlorine to be introduced is 0.01 to 0.4, preferably 0.01 to 0.2 mole/hour per mole of xylene or the compound resulting from the partial chlorine-substitution of its methyl groups present before the initiation of the reaction in the case of a batchwise operation. In the case of a continuous operation, the suitable amount of chlorine is 0.01 to 0.9 mole/hour per mole of xylene or the compound resulting from the partial chlorine-substitution of its methyl groups. It is desirable to avoid the introduction of a large excess of chlorine. The temperature employed for the second-step post chlorination is generally 80° to 160° C in the case of chlorinating m-xylene or the compound resulting from the partial chlorine-substitution of its methyl groups, and 110° to 160° C in the case of chlorinating p-xylene or the compound resulting from the partial chlorine-substitution of its methyl groups. But in order to increase the yield of the hexachloroxylene, the temperature employed for the second-step post chlorination is preferably 100° to 150° C in the case of chlorinating m-xylene or the compound resulting from the partial chlorine-substitution of its methyl groups, and 120° to 150° C in the case of p-xylene or the compound resulting from the partial chlorine-substitution of its methyl groups.

Preferred embodiments of the present invention are described below.

When the production of hexachloroxylene is performed by a batchwise method in the process of this invention, xylene or a compound resultinf from the partial chlorine-substitution of its methyl groups and a predetermined amount of hexachloroxylene as a solvent are mixed within a reactor, and the temperature of the reaction mixture is elevated to a predetermined point. Then, under the irradiation of light containing ultraviolet rays, a chlorine gas is blown into the reactor. Soon after the introduction of the chlorine gas, the reaction begins with the releasing of hydrogen chloride. Then, the reaction is carried out while maintaining the reaction system at a predetermined temperature. During the reaction, it is preferred to adjust the amount of chlorine introduced so that there is no loss of a large amount of unreacted chlorine from a gas exhaust opening and the reaction system can be maintained at a predetermined reaction temperature. In the early stage of the reaction, the progress of the reaction is very rapid, and when the amount of chlorine is large, high heat is generated. Thus, in order to remove the heat of reaction, the reaction mixture needs to be cooled. However, as the reaction proceeds, the reaction speed gradually decreases and the temperature falls. In order to maintain the reaction temperature at a predetermined point, therefore, it is necessary to heat the reaction system. The time when absorption of chlorine substantially ends with a decrease in the rate of reaction is the point at which the first-step chlorination reaction has substantially ended. A gas-chromatographic analysis of the reacton mixture at this point shows that there is almost no intermediate compound convertible to hexachloroxylene by further chlorination. According to the process of this invention, the reaction mixture at this stage is further subjected to a second-step post chlorination reaction under the irradiation of light containing ultraviolet rays while adjusting the reaction time, the amount of chlorine introduced, and the temperature of the reaction mixture as required. It is undesirable to subject the reaction mixture to chlorinating conditions for long periods of time while introducing too much chlorine in the post chlorination step, because it will further cause byproducts as a result of the chlorination of the benzene nucleus of the hexachloroxylene, and result in a reduced yield of hexachloroxylene.

An embodiment of performing the process of this invention continuously will be described below with reference to the case of using three reactors connected in series.

A greater part of the first-step main chlorination reaction is carried out in a first reactor. In this reactor, hexachloroxylene is placed in advance, and while maintaining the temperature of the inside of the reactor at a predetermined point, xylene or a compound resulting from the partial chlorine-substitution of its methyl groups, and chlorine are continuously introduced into the reactor at such a speed that the concentration of hexachloroxylene in the reactor can be maintained at a predetermined value, and the xylene or its derivative is chlorinated under the irradiation of light containing ultraviolet rays. Simultaneously, a part of the reaction mixture is continuously withdrawn from the reactor. The residence time of the reaction mixture in the first reactor varies depending, for example, upon the characteristics of the reactor or the concentration of the hexachloroxylene in the reactor. The general residence time of the reaction mixture is b 4 to 30 hours, preferably 6 to 20 hours. In a second reactor, chlorination to complete the first-stage main chlorination reaction is carried out. The reaction mixture withdrawn from the first reactor is introduced into the second reactor, and reacted by introducing chlorine under the irradiation of light containing ultraviolet rays while maintaining the reaction temperature at a predetermined point. Preferably, the amount of chlorine to be introduced into the second reactor is generally somewhat smaller than that of chlorine introduced into the first reactor. The residence time of the reaction mixture in the second reactor differs according, for example, to the amounts of the reaction intermediates in the reaction mixture introduced from the first reactor or the amount of chlorine introduced, but usually, it is preferably adjusted to 0.5 to 3.0 hours. In the second reactor, the amount of chlorine introduced and the residence time of the reaction mixture are either increased or decreased according to the amounts of the reaction intermediates in the reaction mixture introduced from the first reactor, and the reaction is carried out until its is almost complete. A part of the reaction mixture in the second reactor is continuously withdrawn at such a speed that the amount of the reaction mixture in the second reactor is maintained constant, and then introduced into a third reactor. In the third reactor, post chlorination of the reaction mixture is carried out so as to permit an easy purifying operation. The post chlorination is performed by causing the reaction mixture to reside in the reactor for a predetermined period of time under the irradiation of light containing ultraviolet rays while maintaining the reaction temperature at a predetermined point and blowing chlorine into the reactor at a predetermined rate. When the amount of chlorine is too large, side-reaction may occur, and care is required in this regard.

Alternatively, the use of the third reactor may be omitted, and the first-step chlorination reaction is substantially completed in the first reactor by maintaining the concentration of hexachloroxylene at a high level in the first reactor, and then by properly selecting the reaction conditions in the second reactor, the main chlorination reaction can be completed and the post chlorination reaction can be performed both in the second reactor. According to still another example, the reaction in the second reactor and the subsequent reaction are carried out in three or more reactors, and the overall process of this invention is performed in four or more reactors. The gas discharged from the second and subsequent reactors may be separately treated, or may be blown into the reaction mixture in the first reactor to utilize chlorine effectively.

The reaction mixture obtained by the process of this invention can easily be purified to hexachloroxylene of high purity by removing the chlorine and hydrogen chloride therein, and then distilling it at reduced pressure.

An aromatic dicarboxylic acid chloride can be produced by reacting the resulting hexachloroxylene with a corresponding aromatic dicarboxylic acid by a method known per se. Specifically, in accordance with the reaction of equation (II), isophthaloyl dichloride can be prepared by reacting $\alpha, \alpha, \alpha, \alpha', \alpha', \alpha'$-hexachloro-m-xylene with isophthalic acid, and terephthaloyl dichloride, by reacting 60 , $\alpha, \alpha, \alpha', \alpha', \alpha'$-hexachloro-p-xylene with terephthalic acid.

In this reaction, the aromatic dicarboxylic acid is used preferably in an amount of 1 mole or slightly larger than 1 mole per mole of the hexachloroxylene. When the hexachloroxylene is used in excess of the aromatic dicarboxylic acid, the hexachloroxylene remains unreacted, or a compound containing a trichloromethyl group is formed. These compounds are difficult to separate by distillation since their boiling points are almost the same as the boiling point of the aromatic dicarboxylic acid chloride as a final product. On the other hand, when the aromatic dicarboxylic acid is used in a large excess with respect to hexachloroxylene, the resulting aromatic dicarboxylic acid chloride forms a condensate together with the remaining aromatic dicarboxylic acid, and since there is no more hexachloroxylene to be reacted with it, the condensate is present as such and reduces the yield of the aromatic dicarboxylic acid chloride. Accordingly, the amount of the aromatic dicarboxylic acid to be used is 1.00 to 1.10, preferably 1.01 to 1.04, moles per mole of the hexachloroxylene.

The reaction between the hexachloroxylene and the aromatic dicarboxylic acid is catalyzed by a Friedel-Crafts catalyst such as aluminum chloride, antimony chloride, ferric chloride, tin tetrachloride, titanium tetrachloride, bismuth chloride or zinc chloride. Of these, ferric chloride is especially preferred. The amount of the catalyst is 0.01 to 0.5% by weight based on the mixture of the aromatic dicarboxylic acid and hexachloroxylene.

In the reaction between hexachloroxylene and aromatic dicarboxylic acid, the reaction temperature is 50° to 150° C in the case of producing isophthaloyl dichloride, and 120° to 180° C in the case of producing terephthaloyl dichloride. The reaction is continued until insoluble components such as the aromatic dicarboxylic acid disappear, and the generation of hydrogen chloride is hardly observed. The quality of the resulting isophthaloyl dichloride or terephthaloyl dichloride can be elevated by purification.

Aromatic dicarboxylic acid chlorines produced by reacting the high purity hexachloroxylene obtained by the process of this invention and an aromatic dicarboxylic acid have very superior suitability as a raw material for the production of thermally stable polymers such as aromatic polyamides or aromatic polyesters. As will be shown in Example 6 to be given later on, the suitability of the aromatic dicarboxylic acid chloride as a raw material for thermally stable polymer is closely related with the freezing point of the aromatic dicarboxylic acid chloride measured by the method of JIS K 4101.

The following examples illustrate the present invention more specifically.

EXAMPLE 1

A. A 2-liter flask equipped with a thermometer, a chlorine introducing tube and a reflux condenser concurrently acting as a gas exhausting means was charged with 400 g (3.77 moles) of m-xylene and 800 g of $\alpha, \alpha, \alpha, \alpha', \alpha', \alpha'$-hexachloro-m-xylene, and the contents were heated to 130° C. Under the irradiation of light from a 100 W internally irradiating high pressure mercury lamp, chlorine gas was blown into the flask while stirring the contents of the flask by an electromagnetically operated stirrer. The amount of chlorine blown was adjusted to about 269.8 g/hour (3.8 moles/hour) during the first 5 hours, and after a lapse of the 5-hour period, the reaction was carried out for an additional 3 hours while blowing chlorine at a somewhat decreased rate. Specifically, during the 3-hour period, the amount of chlorine was adjusted to about 277 g/hour for the first one hour, 174 g/hour for the next one hour, and about 120 g/hour for the last one hour. A gas-chromatographic analysis of the reaction mixture sampled at this time showed that there was hardly any reaction intermediate convertible to $\alpha, \alpha, \alpha, \alpha', \alpha', \alpha'$-hexachloro-m-xylene by further chlorination. The amount of chlorine blown was changed at this time to 30 g/hour (0.42 mole/hour), and under the irradiation of the light, the reaction was carried out further for one hour at 130° C. After the reaction, dry nitrogen gas was passed through the flask to remove the chlorine and hydrogen chloride gas present in the reaction system, and then, 1973 g of the reaction mixture was obtained. A gas-chromatographic analysis of this reaction mixture showed that the concentration of 60, $\alpha, \alpha, \alpha', \alpha', \alpha', \alpha'$-hexachloro-m-xylene was 98.6% by weight.

When the amount of $\alpha, \alpha, \alpha, \alpha', \alpha', \alpha'$-hexachloro-m-xylene remaining after removing 800 g of the initially fed $\alpha, \alpha, \alpha, \alpha', \alpha', \alpha'$-hexachloro-m-xylene was assumed to be that of the hexachloro-m-xylene newly formed, the yield of the $\alpha, \alpha, \alpha, \alpha', \alpha', \alpha'$-hexachloro-m-xylene based on m-xylene was 97.1%.

The crude $\alpha, \alpha, \alpha, \alpha', \alpha', \alpha'$-hexachloro-m-xylene so obtained was distilled at reduced pressure using an about 60 cm-long column packed with procelain Raschig rings. The first and last fractions were removed, and a fraction boiling at 154° to 158° C under 10 mmHg was recovered. The amount of the recovered fraction was about 85% of the amount of the crude product initially charged. A gas-chromatographic analysis of this fraction showed that the purity of $\alpha, \alpha, \alpha, \alpha', \alpha', \alpha'$-hexachloro-m-xylene was more than 99.8%.

B. A mixture consisting of 313 g (1.00 mole) of the purified $\alpha, \alpha, \alpha, \alpha', \alpha', \alpha'$-hexachloro-m-xylene obtained in (A) above, 168 g (1.01 moles) isophthalic acid and 0.48 g of anhydrous ferric chloride was heated with stirring, since hydrogen chloride gas began to form at a temperature of about 60° C, the reaction was carried out for about 40 minutes at this temperature. Over the course of about 30 minutes, the reaction temperature was raised to 100° C, and the reaction was further carried out for 20 minutes at 100° C to complete it. The crude product was distilled at 118° to 121° C and 5 mmHg using an about 20 cm-lone Vigreaux column to afford 386 g of isophthaloyl dichloride. The yield of the isophthaloyl dichloride based on the $\alpha, \alpha, \alpha, \alpha', \alpha', \alpha'$-hexachloro-m-xylene was 95.0%. The freezing point of the isophthaloyl dichloride was 43.68° C.

EXAMPLE 2

A. The same chlorination reactor as used in Example 1 was charged with 400 g (3.77 mole) of m-xylene and 800 g of the crude reaction mixture obtained in Example 1, (A), and the reaction was performed by the same procedure as in Example 1, (A). After the reaction, chlorine and hydrogen chloride present in the reaction mixture were removed, and 1971 g of the reaction mixture was obtained. A gas-chromatographic analysis of the reaction mixture showed that the concentration of $\alpha, \alpha, \alpha, \alpha', \alpha', \alpha'$-hexachloro-m-xylene was 97.7% by weight.

The resulting crude $\alpha, \alpha, \alpha, \alpha', \alpha', \alpha'$-hexachloro-m-xylene so obtained was distilled at reduced pressure using an about 60 cm-long column packed with porcelain Raschig rings. The first and last fractions were removed, and a fraction boiling at 154° to 158° C under 10 mmHg was recovered. The amount of this fraction was about 84% based on the amount of the crude product initially charged.

A gas-chromatographic analysis of this fraction showed that the purity of $\alpha, \alpha, \alpha, \alpha', \alpha', \alpha'$-hexachloro-m-xylene was more than 99.8%.

B. A mixture consisting of 313 g (1.00 mole) of the purified $\alpha, \alpha, \alpha, \alpha', \alpha', \alpha'$-hexachloro-m-xylene obtained in (A) above, 168 g (1.01 moles) of isophthalic acid and 0.48 g of anhydrous ferric chloride was heated with stirring, and the same reaction as in Example 1, (B) was carried out.

The resultinf crude product was distilled at 118° to 121° C and 5 mmHg using an about 20 cm-long Vigreaux column to afford 384 g of isophthaloyl dichloride. The yield of the isophthaloyl dichloride based on the $\alpha, \alpha, \alpha, \alpha', \alpha', \alpha'$-hexachloro-m-xylene was 94.6%. The isophthaloyl dichloride was found to have a freezing point of 43.67° C.

COMPARATIVE EXAMPLE 1

A. The same chlorination reactor as used in Example 1 was charged with 680 g (6.40 moles) of m-xylene, and the contents were heated to 130° C. Chlorine was introduced into the reactor while irradiating light from a 100 W internally irradiating high pressure mercury lamp, and the reaction was carried out with stirring. The amount of chlorine blown was about 454 g/hour (6.4 moles/hour) during the first 5 hours. After the lapse of the 5-hour period, the amount of chlorine was somewhat decreased, and the reaction was performed for an additional 3 hours. The amount of chlorine was adjusted to about 386 g/hour for the first one hour, about 295 g/hour for the next one hour, and about 204 g/hour for the last one hour. After the reaction, dry nitrogen gas was passed through the flask to remove chlorine and hydrogen chloride present in the reaction system, and then 1965 g of the reaction mixture was obtained. A gas-chromatographic analysis of this reaction mixture showed that the concentration of $\alpha, \alpha, \alpha, \alpha', \alpha', \alpha'$-hexachloro-m-xylene was 90.2% by weight. The amount of $\alpha, \alpha, \alpha, \alpha', \alpha', \alpha'$-hexachloro-m-xylene obtained was 1772 g, and its yield based on m-xylene was 88.5%.

As compared with the results obtained in Examples 1 and 2, the purity of the resulting crude $\alpha, \alpha, \alpha, \alpha', \alpha', \alpha'$-hexachloro-m-xylene was low, and its yield based on m-xylene was also low.

The crude $\alpha, \alpha, \alpha, \alpha', \alpha', \alpha'$-hexachloro-m-xylene so obtained was distilled at reduced pressure using an about 60 cm-long column packed with porcelain Raschig rings. The first and last fractions were removed, and a fraction boiling at 154° to 158° C under 10 mmHg was recovered. The amount of this fraction recovered was 75% based on the amount of the crude product initially charged.

A gas-chromatographic analysis of this fraction showed that the purity of $\alpha, \alpha, \alpha, \alpha', \alpha', \alpha'$-hexachloro-m-xylene was 99.1%.

B. A mixture consisting of 313 g (1.00 mole) of the purified $\alpha, \alpha, \alpha, \alpha', \alpha', \alpha'$-hexachloro-m-xylene obtained in (A) above, 168 g (1.01 moles) of isophthalic acid and 0.48 g of anhydrous ferric chloride was reacted in the same way as in Example 1, (B). After the reaction, the crude product was distilled at 118° to 121° C and 5 mmHg using an about 20 cm-long Vigreaux column to afford 382 g of isophthaloyl dichloride. The yield of the isophthaloyl dichloride based on the $\alpha, \alpha, \alpha, \alpha', \alpha', \alpha'$-hexachloro-m-xylene was 94.1%, and its freezing point was 43.6° C.

The freezing point of the resulting isophthaloyl dichloride was lower than those of the products obtained 3 in Examples 1 and 2.

COMPARATIVE EXAMPLE 2

A. The same chlorination reactor as used in Example 1 was charged with 400 g (3.77 moles) of m-xylene and 800 g of $\alpha, \alpha, \alpha, \alpha', \alpha', \alpha'$-hexachloro-m-xylene, and the contents were heated to 130° C. Chlorine was blown into the flask with stirring while irradiating light from a 100 W internally radiating high pressure mercury lamp, and the reaction was carried out. The amount of chlorine blown was adjusted to 269.8 g./hour (3.8 moles/hour) during the first 5 hours, and after the lapse of the 5-hour period, the amount of chlorine fed was decreased in the same way as in Example 1, and the reaction was carried out for an additional 3 hours. After the reaction, dry nitrogen gas was passed through the reactor to remove chlorine and hydrogen chloride present in the reaction system, and 1970 g of the reaction mixture was obtained. A gas-chromatographic analysis of this reaction mixture showed that no reaction intermediate convertible to $\alpha, \alpha, \alpha, \alpha', \alpha', \alpha'$-hexachloro-m-xylene by further chlorination was present in the reaction mixture, and the concentration of the $\alpha, \alpha, \alpha\alpha', \alpha', \alpha'$-hexachloro-m-xylene was 98.7% by weight.

The crude $\alpha, \alpha, \alpha, \alpha', \alpha', \alpha'$-hexachloro-m-xylene so obtained was distilled at reduced pressure using an about 60 cm-long column packed with porcelain Raschig rings. The first and last fractions were removed, and a fraction boiling at 154° to 158° C under 10 mmHg was recovered. The amount of this fraction was about 84% based on the amount of the crude product initially charged. A gas-chromatographic analysis of this fraction showed that the purity of $\alpha, \alpha, \alpha, \alpha', \alpha', \alpha'$-hexachloro-m-xylene was 99.2%.

B. A mixture consisting of 313 g (1.00 mole) of the purified $\alpha, \alpha, \alpha, \alpha', \alpha', \alpha'$-hexachloro-m-xylene obtained in (A) above, 168 g (1.01 moles) of isophthalic acid and 0.48 g of anhydrous ferric chloride was heated with stirring, and reacted in the same way as in Example 1, (B).

The crude product obtained as a result of the reaction was distilled at 118° to 121° C under 5 mmHg using an about 20 cm-long Vigreaux column to afford 384 g of isophthaloyl dichloride as a distillate. The yield of the isophthaloyl dichloride was 94.6% based on $\alpha, \alpha, \alpha, \alpha', \alpha', \alpha'$-hexachloro-m-xylene. This product had a freezing point of 43.48° C.

EXAMPLE 3

A. A 2-liter flask equipped with a thermometer, a chlorine introducing tube, a reflux condenser concurrently acting as a gas exhaust means, and an internally irradiating high pressure mercury lamp having a double cooling tube, was charged with 425 g (4.00 moles) of p-xylene and 700 g. of $\alpha,\alpha,\alpha,\alpha',\alpha',\alpha'$-hexachloro-p-xylene, and the contents were heated to 135° C. Chlorine was blown into the reactor with stirring while irradiating light from a 100 W high pressure mercury lamp. The amount of chlorine blown was adjusted to about 284 g/hour (4.0 moles/hour) during the first 5 hours. After the lapse of the 5-hour period, the amount of chlorine introduced was somewhat reduced, and the reaction was performed for an additional 3 hours. Specifically, the amount of chlorine was adjusted to about 255 g/hour for the first one hour, about 199 g/hour for the next one hour, and about 170 g/hour for the last one hour. A gas-chromatographic analysis of the reaction mixture at this time showed that there is hardly any reaction intermediate convertible to $\alpha,\alpha,\alpha,\alpha',\alpha',\alpha'$-hexachloro-p-xylene by further chlorination.

From this time, the amount of chlorine blown into the reactor was changed to 40 g/hour (0.56 mole/hour), and the reaction was further carried out for one hour at 135° C under the irradiation of light. After the chlorination reaction, a dry nitrogen gas was passed through the reactor to remove chlorine and hydrogen chloride present in the reaction system, and 1941 g of the reaction mixture was obtained. A gas-chromatographic analysis of this reaction mixture showed that the concentration of $\alpha,\alpha,\alpha,\alpha',\alpha',\alpha'$-hexachloro-p-xylene was 98.4% by weight.

When the amount of the $\alpha,\alpha,\alpha,\alpha',\alpha',\alpha'$-hexachloro-p-xylene remaining after removing 700 g of the $\alpha,\alpha,\alpha,\alpha',\alpha',\alpha'$-hexachloro-p-xylene initially charged into the reactor was assumed to be that of the hexachloro-p-xylene newly formed, the yield of $\alpha,\alpha,\alpha,\alpha',\alpha',\alpha'$-hexachloro-p-xylene based on p-xylene was 96.7%.

The crude $\alpha,\alpha,\alpha,\alpha',\alpha',\alpha'$-hexachloro-p-xylene so obtained was distilled at reduced pressure using an about 60 cm-long column packed with porcelain Raschig rings. The first and last fractions were removed, and a fraction boiling at 158° to 162° C under 10 mmHg was recovered. The amount of this fraction was about 85% of the crude product initially charged. A gas-chromatographic analysis of this fraction showed that the purity of the $\alpha,\alpha,\alpha,\alpha',\alpha',\alpha'$-hexachloro-p-xylene was more than 99.8%.

B. A mixture consisting of 313 g (1.00 mole) of the purified $\alpha,\alpha,\alpha,\alpha',\alpha',\alpha'$-hexachloro-p-xylene, 169.5 g (1.02 moles) of terephthalic acid and 0.38 g of anhydrous ferric chloride was heated with stirring, and reacted for one hour at about 130° C. Then, the temperature was raised to 140° C, and the reaction was performed at this temperature for 20 minutes to complete it.

The resulting crude product was distilled at 117° to 121° C and 5 mmHg using an about 20 cm-long Vigreaux column to afford 382 g of terephthaloyl dichloride. The yield of the terephthaloyl dichloride based on $\alpha,\alpha,\alpha,\alpha',\alpha',\alpha'$-hexachloro-p-xylene was 91.1%, and its freezing point was 81.53° C.

COMPARATIVE EXAMPLE 3

A. The same chlorination reactor as used in Example 3 was charged with 680 g (6.40 moles) of p-xylene, and the contents were heated to 135° C. Chlorine was introduced with stirring while irradiating light from a 100 W high pressure mercury lamp. The amount of chlorine introduced was adjusted to about 454 g/hour (6.4 moles/hour) during the first 5 hours, and after the lapse of the 5-hour period, the reaction was performed for an additional 3 hours at a somewhat reduced rate of chlorine introduction. Specifically, the amount of chlorine blown was adjusted to about 408 g/hour for the first one hour, about 318 g/hour for the next one hour, and about 272 g/hour for the last one hour. After the reaction, a dry nitrogen gas was passed through the reactor to remove chlorine and hydrogen chloride present in the reaction system, and 1960 g of the reaction mixture was obtained. A gas-chromatographic analysis of the reaction mixture showed that the concentration of the $\alpha,\alpha,\alpha,\alpha',\alpha',\alpha'$-hexachloro-p-xylene was 93.2% by weight. The amount of the resulting $\alpha,\alpha,\alpha,\alpha',\alpha',\alpha'$-hexachloro-p-xylene was 1827 g, and its yield based on p-xylene was 91.2%.

The resulting crude $\alpha,\alpha,\alpha,\alpha',\alpha',\alpha'$-hexachloro-p-xylene so obtained was distilled at reduced pressure using an about 60 cm-long column packed with porcelain Raschig rings. The first and last fractions were removed, and a fraction boiling at 158° to 162° C under 10 mmHg was recovered. The amount of this fraction was 76% based on the crude product initially charged. A gas-chromatographic analysis of this fraction showed that the purity of $\alpha,\alpha,\alpha,\alpha',\alpha',\alpha'$-hexachloro-p-xylene was 99.2%.

B. A mixture consisting of 313 g (1.00 mole) of the purified $\alpha,\alpha,\alpha,\alpha',\alpha',\alpha'$-hexachloro-p-xylene obtained in A. above, 169.5 g (1.02 moles) of terephthalic acid and 0.38 g of anhydrous ferric chloride was heated with stirring, and reacted in the same way as in Example 3, (B).

The crude product obtained was distilled at 117° to 121° C and 5 mmHg using an about 20 cm-long Vigreaux column to afford 384 g of terephthaloyl dichloride. The yield of the terephthaloyl dichloride was 94.6% based on the $\alpha,\alpha,\alpha,\alpha',\alpha',\alpha'$-hexachloro-p-xylene. It had a freezing point of 81.28° C.

COMPARATIVE EXAMPLE 4

A. The same chlorination reactor as used in Example 3 was charged with 425 g (4.00 moles) of p-xylene and 700 g of $\alpha,\alpha,\alpha,\alpha',\alpha',\alpha'$-hexachloro-p-xylene, and the contents were heated to 135° C. Chlorine was introduced into the reactor with stirring while irradiating light from a 100 W internally irradiating high pressure mercury lamp. The amount of chlorine introduced was adjusted to 284 g/hour (4.0 moles/hour) during the first 5 hours, and after the lapse of the 5-hour period, the reaction was performed for an additional 3 hours at the same reduced rate of chlorine introduction as in Example 3. After the reaction, a dry nitrogen gas was passed through the reactor to remove chlorine and hydrogen chloride present in the reaction system, and 1939 g of the reaction mixture was obtained. A gas-chromatographic analysis of the reaction mixture showed that no reaction intermediate convertible to $\alpha,\alpha,\alpha,\alpha',\alpha',\alpha'$-hexachloro-p-xylene by further chlorination was present, and the concentration of $\alpha,\alpha,\alpha,\alpha',\alpha',\alpha'$-hexachloro-p-xylene was 98.6% by weight.

The crude $\alpha,\alpha,\alpha,\alpha',\alpha',\alpha'$-hexachloro-p-xylene obtained was distilled at reduced pressure using an about 60 cm-long column packed with porcelain Raschig rings. The first and last fractions were removed, and a fraction boiling at 158° to 162° C under 10 mmHg was recovered. The amount of this fraction was about 83% of the crude product initially charged. A gas-chromatographic analysis of this reaction mixture showed that the purity of $\alpha,\alpha,\alpha,\alpha',\alpha',\alpha'$-hexachloro-p-xylene was 99.3%.

B. a mixture consisting of 313 g (1.00 mole) of the purified $\alpha,\alpha,\alpha,\alpha',\alpha',\alpha'$-hexachloro-p-xylene obtained in (A) above, 169.5 g (1.02 moles) of terephthalic acid and 0.38 g of anhydrous ferric chloride was heated with stirring, and reacted in the same way as in Example 3, (B).

The resulting crude product was distilled at 117° to 121° C and 5 mmHg using an about 20 cm-long Vigreaux column to afford 382 g of terephthaloyl dichloride. The yield of the terephthaloyl dichloride based on the α,α,α,α',α',α'-hexachloro-p-xylene was 94.1%. It had a freezing point of 81.30° C.

EXAMPLE 4

A. A 2-liter glass reactor equipped with a light irradiating device, a thermometer, a stirrer, a reflux condenser concurrently acting as a gas exhaust means, a chlorine introducing inlet, a feed opening and an opening for overflowing the reaction mixture was used as a first reactor. A 700 ml. reactor having the same accessory devices as in the first reactor was used as a second reactor and provided at a position slightly below the first reactor. A 250 ml. reactor having the same devices as in the first reactor was used as a third reactor and positioned at a point just a little bit lower than the second reactor. The overflowing opening of the first reactor and the feed opening of the second reactor were connected to each other. Likewise, the overflowing opening of the second reactor was connected to the feed opening of the third reactor, so that the reaction mixture which overflowed from one reactor was fed into the next reactor beneath it. The capacity of the first reactor up to the overflowing opening was 1.8 liters, and the capacities of the second and third reactors up to the overflowing openings were 500 ml, and 180 ml, respectively.

In operation, each of these reactors was filled with α,α,α,α',α',α'-hexachloro-m-xylene, and the contents of each reactor were heated to 135° C. At this temperature, m-xylene was fed into the first reactor at a rate of 116 g/hour (1.09 moles/hour) under the irradiation of light while stirring the contents. The m-xylene had been preheated to 120° to 130° C prior to feeding into the first reactor. Chlorine gas was blown into the bottom of each of the reactors at a rate of about 550 g/hour (7.87 moles/hour) (into the first reactor), about 120 g/hour (1.69 moles/hour) (into the second reactor), and about 20 g/hour (0.28 mole/hour) (into the third reactor).

The gas released from the reactors was conducted out of the system from the top of the condenser. The reaction mixture which increased in volume as a result of the feeding and reaction of m-xylene was overflowed, and conducted to the next reactor. The reaction mixture which overflowed from the third reactor was conducted to a reservoir for storing the reaction mixture.

The reaction was performed in this manner for 48 hours, and the reaction mixture in each of the reactors was analyzed by gas chromatography. The composition of each reaction mixture is shown in Table 1.

In the same way, the reaction was performed subsequently for 20 hours. During this time, 2315 g (21.81 moles) of m-xylene and 11.14 Kg (157.09 moles) of chlorine were fed into the first reactor, 2.40 Kg (33.85 moles) of chlorine into the second reactor, and 400 g (5.64 moles) of chlorine into the third reactor. After the reaction, the chlorine and hydrogen chloride present in the reaction mixture were removed, and 6.78 Kg of the reaction mixture was obtained. A gas-chromatographic analysis of this reaction mixture showed that the concentration of α,α,α,α',α',α'-hexachloro-m-xylene was 96.4% by weight. The analysis results showed that during a 20-hour period (from 48 hours to 68 hours), 6536 of α,α,α,α',α',α'-hexachloro-m-xylene was formed. The yield was 95.8% based on m-xylene.

The crude α,α,α,α',α',α'-hexachloro-m-xylene so obtained was distilled at reduced pressure using an about 60 cm-long column packed with porcelain Raschig rings. The first and last fractions were removed, and a fraction boiling at 154° to 158° C under 10 mmHg was recovered. The amount of this fraction was about 85% based on the amount of the crude product initially charged. A gas-chromatographic analysis of this fraction showed that the purity of the α,α,α,α',α',α'-hexachloro-m-xylene was more than 99.8%.

B. A mixture consisting of 313 g (1.00 mole) of the purified α,α,α,α',α',α'-hexachloro-m-xylene obtained in (A) above, 168 g (1.01 moles) of isophthalic acid and 0.48 g of anhydrous ferric chloride was heated with stirring, and reacted in the same way as in Example 1, (B).

The resulting crude reaction product was distilled at 118° to 121° C and 5 mmHg using an about 20 cm-long Vigreaux column to afford 388 g of isophthaloyl dichloride. Its yield based on the α,α,α,α',α',α'-hexachloro-m-xylene was 95.6%. The isophthaloyl chloride had a freezing point of 43.68° C.

Table 1

Composition of the reaction mixture in each reactor at the end of 48 hours after the initiation of the reaction (% by weight)

| Ingredients | First reactor | Second reactor | Third reactor |
| --- | --- | --- | --- |
| m-Xylene | 0.02 | — | — |
| α-Chloro-m-xylene | 0.3 | — | — |
| α,α'-Dichloro-m-xylene | 0.8 | — | — |
| α,α,α'-Trichloro-m-xylene | 1.7 | — | — |
| α,α,α',α'-Tetrachloro-m-xylene | 5.0 | — | — |
| α,α,α,α'-Pentachloro-m-xylene | 9.1 | — | — |
| α,α,α,α',α',α'-Hexachloro-m-xylene | 79.6 | 96.3 | 96.1 |
| Others | 3.5 | 3.7 | 3.9 |

COMPARATIVE EXAMPLE 5

A. In the side-chain chlorination of m-xylene by the method of Example 4, (A), the reaction mixture from the second reactor was analyzed by gas-chromatography, and it was found that the concentration of α,α,α,α',α',α'-hexachloro-m-xylene was 96.5% by weight, and there was hardly any intermediate convertible to α,α,α,α',α',α'-hexachloro-m-xylene by further chlorination. This reaction mixture was distilled at reduced pressure using an about 60 cm-long column packed with porcelain Raschig rings. The first and last fractions were removed, and a fraction boiling at 154° to 158° C under 10 mmHg was recovered. The amount of this fraction was about 85% based on the amount of the crude reaction mixture initially charged. A gas-chromatographic analysis of this fraction showed that the purity of α,α,α,α',α',α'-hexachloro-m-xylene was 99.2%.

B. The α,α,α,α',α',α'-hexachloro-m-xylene obtained in (A) above was reacted with isophthalic acid in the same way as in Example 1, (B) to afford isophthaloyl dichloride in a yield of 95.2% based on the α,α,α,α',α'-hexachloro-m-xylene. The isophthaloyl dichloride had a freezing point of 43.42° C.

EXAMPLE 5

A. A 2-liter glass reactor and a 500 ml glass reactor were used as a first and a second reactor, and disposed in the same way as in Example 4, (A). The capacity of the reactor up to the overflowing opening was 1.8 liters in the first reactor, and 400 ml in the second reactor. Each of the reactors was filled with α, α, α, α', α', α'-hexachloro-p-xylene, and it was heated to 130° C. At this temperature, p-xylene and chlorine were continuously fed and reacted under the irradiation of light in the same way as in Example 4.

At this time, the p-xylene was fed into the first reactor at a rate of about 81 g/hour (0.763 mole), and chlorine was fed at a rate of 390 g/hour (5.50 moles/hour) into the first reactor and at a rate of 40 g/hour (0.56 mole/hour) into the second reactor.

The reaction was performed in this manner for 40 hours, and the reaction mixture in the first reactor was analyzed by gas-chromatography. It was found that the concentrations of α,α,α,α',α',α'-hexachloro-p-xylene was 97.5% by weight.

In the same way, the reaction was performed for an additional 20 hours. During this time, 1626 g (15.32 moles) of p-xylene and 7796 g (109.9 moles) of chlorine were fed into the first reactor, and 795 g (11.2 moles) of chlorine was fed into the second reactor. After the reaction, the chlorine and hydrogen chloride present in the reaction system were removed, and 4756 g of the reaction mixture was obtained. A gas-chromatographic analysis of this reaction mixture showed that the concentration of α,α,α,α',α',α'-hexachloro-p-xylene was 97.2% by weight. The results of analysis showed that during a 20-hour period (from 40 to 60 hours), 4623 g of α,α,α,α',α',α'-hexachloro-p-xylene was formed. This corresponded to a yield of 96.5% based on p-xylene.

The resulting crude α,α,α,α',α',α'-hexachloro-p-xylene was distilled at reduced pressure using an about 60 cm-long column packed with porcelain Raschig rings. The first and last fractions were removed, and a fraction boiling at 158° to 162° C under 10 mmHg was recovered. The amount of this fraction was about 85% based on the amount of the crude product initially charged.

A gas-chromatographic analysis of this fractions showed that the purity of α,α,α,α',α',α'-hexachloro-p-xylene was more than 99.8%.

B. The α,α,α,α',α',α'-hexachloro-p-xylene obtained in (A) above was reacted with terephthalic acid in the same way as in Example 3, (B) to afford 384 g of terephthaloyl dichloride. Its yield was 94.6% based on α,α,α,α',α',α'-hexachloro-p-xylene, and the terephthaloyl dichloride had a freezing point of 81.54° C.

EXAMPLE 6

Each of the aromatic dicarboxylic acid chlorides obtained in the above examples was reacted with an aromatic diamine under predetermined standard polymerization conditions to produce aromatic polyamides. The degrees of polymerization (expressed in terms of viscosity) of the resulting polyamides were measured, and the suitability of the aromatic dicarboxylic acid chlorides as raw materials for polymers was evaluated on the basis of the degree of polymerization.

The standard polymerization conditions and the method for measuring the viscosities differed somewhat between isophthaloyl dichloride and terephthaloyl dichloride, and are shown below.

A. Isophthaloyl dichloride
Test method

In a 300 ml well-dried three-necked flask, 12.98 g (0.1200 mole) of m-phenylene diamine was placed, and dissolved in N-methylpyrrolidone with a water content of about 0.01% to form a uniform solution. The solution was cooled to −20° C, and 24.38 g (0.1201 mole) of isophthaloyl dichloride to be tested was added to the solution while stirring it at a speed of about 200 rpm. The temperature of the contents of the flask rose abruptly with the addition of the isophthaloyl dichloride. The addition was completed within 5 minutes while controlling the temperature of the contents of the flask so that it did not exceed 40° C. The resulting non-transparent viscous solution was heated at 40° C for about 3 hours with stirring, and then added to 2 liters of cold water, followed by stirring for about 15 minutes. The precipitated polymer was filtered, washed with 2 liters of warm water at about 60° C, and dried.

The resulting polymer was dissolved in 95% by weight sulfuric acid, and its relative viscosity ($\eta_{rel}$) was measured by a viscometer at 25° C in a concentration of 1 g/100 ml $H_2SO_4$.

$$\eta_{rel} = \frac{\text{Falling time in seconds of the sample solution}}{\text{Falling time in seconds of the 95\% sulfuric acid}}$$

In order that the resulting polymers have good stretchability and spinnability, they would desirably have a relative viscosity of at least 3.00.

The test results obtained with regard to the isophthaloyl dichlorides obtained in the above examples are shown in Table 2.

Table 2

| Samples | Freezing point (° C) of isophthaloyl dichloride | Relative viscosity of the polymer |
|---|---|---|
| Example 1 | 43.68 | 3.40 |
| Example 2 | 43.67 | 3.36 |
| Example 4 | 43.68 | 3.41 |
| Comparative Example 1 | 43.46 | 2.68 |
| Comparative Example 2 | 43.48 | 2.74 |
| Example 5 | 43.42 | 2.56 |

B. Terephthaloyl dichloride
Test method

A four-necked flask equipped with a nitrogen introducing inlet, a stirring rod and a thermometer was heated by a burner in a stream of nitrogen to remove water adhering to it. 135 ml of N-methylpyrrolidone which had been purified and dried to a substantially anhydrous condition, 65 ml of hexamethyl phosphoric triamide and 3.2453 g (0.0300 mole) of p-phenylenediamine, were precisely weighed, and charged into the flask. A uniform solution was prepared, and the contents of the flask was cooled to 5° C with an ice bath. Then, 6.0927 g (0.0300 mole) of solid terephthaloyl dichloride to be tested was added at a time. When the rise of the contents temperature became 20° C, the ice bath was removed, and the reactions mixture was stirred continuously. When the stirring was continued for about 10 minutes, the reaction misture became abruptly viscous, and then changed to a jelly-like mass. The stirring was stopped, and the jelly-like mass was allowed to stand for about 18 hours.

The resulting jelly-like mass was vigorously stirred in a mixer, pulverized, well washed, and filtered to form a polymer powder. The resulting polymer was thoroughly dried, and dissolved in a conc. sulfuric acid (98% by weight) to form a solution having a concentration of 0.5 g/100 ml. conc. sulfuric acid. At 30° C, the logarithmic viscosity of the polymer was measured for this solution.

$$\text{Logarithmic viscosity} = \frac{\ln \eta_{rel}}{c}$$

wherein $\eta_{rel}$ is $\dfrac{\text{Falling time in seconds of the sample solution}}{\text{Falling time in seconds of conc. sulfuric acid}}$ c is the amount in grams of the polymer dissolved in 100 ml. of conc. sulfuric acid, and 0.5.

In order that the resulting polymers have good stretchability and spinnability, they would desirably have a logarithmic viscosity of at least 5.00, preferably at least 6.00.

The test results obtained with regard to the terephthaloyl dichlorides obtained in the above examples are shown in Table 3.

Table 3

| Samples | Freezing point (° C) of terephthaloyl dichloride | Logarithmic viscosity of the polymer |
| --- | --- | --- |
| Example 3 | 81.53 | 6.57 |
| Example 5 | 81.54 | 6.67 |
| Comparative Example 3 | 81.28 | 4.62 |
| Comparative Example 4 | 81.30 | 4.80 |

The results shown in Tables 2 and 3 clearly demonstrate that aromatic dicarboxylic acid chlorides prepared from the $\alpha,\alpha,\alpha,\alpha',\alpha',\alpha'$-hexachloroxylenes prepared by the process of this invention have far better suitability as materials for polymers than those prepared from the $\alpha,\alpha,\alpha,\alpha',\alpha',\alpha'$-hexachloroxylenes prepared by the process given in the above comparative examples. It can also be seen that the suitability of the aromatic dicarboxylic acid chloride as a material for polymers is closely related to its freezing point, and a slight difference in freezing point exerts a great influence on the degree of polymerization of polymer.

What we claim is:

1. A process for batchwise or continuous production of $\alpha,\alpha,\alpha,\alpha',\alpha',\alpha'$-hexachloroxylene by reacting a xylene compound selected from the group consisting of (i) xylene selected from m-xylene and p-xylene and (ii) compounds resulting from the partial chlorination of the side-chain methyl groups of the xylene (i), with chlorine under the irradiation of ultraviolet rays; said process comprising
   1. a first-step chlorination reaction which is carried out in the presence of $\alpha,\alpha,\alpha,\alpha',\alpha',\alpha'$-hexachloroxylene as a solvent added at the initial stage of the reaction, and continued until a compound convertible to $\alpha,\alpha,\alpha,\alpha',\alpha',\alpha'$-hexachloroxylene by chlorination becomes substantially absent in the reaction mixture, and
   2. a second-step chlorination reaction which is continued from the first-step chlorination and carried out to convert difficulty-separable by-products present in the reaction mixture to easily-separable compounds.

2. The process of claim 1 wherein the amount of the $\alpha,\alpha,\alpha,\alpha',\alpha',\alpha'$-hexachloroxylene added as a solvent at the initial stage of the reaction is 0.3 to 15 times the weight of the starting xylene compound when the process is carried batchwise, and 40 to 99% by weight of the reaction mixture when the process is carried out continuously.

3. The process of claim 1 wherein the concentration of chlorine in the second-step chlorination reaction is lower than that in the first-step chlorination reaction.

4. The process of claim 1 wherein the xylene compound is m-xylene or p-xylene.

5. The process of claim 1 wherein after the end of the second-step chlorination, the reaction mixture is distilled to separate and remove impurities.

* * * * *